US011231325B2

(12) United States Patent
Waldron et al.

(10) Patent No.: US 11,231,325 B2
(45) Date of Patent: Jan. 25, 2022

(54) APPARATUS AND METHOD TO PERFORM PER-PIXEL MICROBOLOMETER CAMERA TIME CONSTANT MEASUREMENTS

(71) Applicant: United States of America, as represented by the Secretary of the Army, Fort Belvoir, VA (US)

(72) Inventors: Dennis L. Waldron, Chesapeake Beach, MD (US); Rolf-Dieter J. Lohrmann, Clifton, VA (US)

(73) Assignee: UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 328 days.

(21) Appl. No.: 16/690,163

(22) Filed: Nov. 21, 2019

(65) Prior Publication Data

US 2021/0156742 A1 May 27, 2021

(51) Int. Cl.
| | |
|---|---|
| *G06K 9/00* | (2006.01) |
| *G01J 5/00* | (2006.01) |
| *A61B 5/01* | (2006.01) |
| *A61B 5/00* | (2006.01) |
| *G06T 7/00* | (2017.01) |

(52) U.S. Cl.
CPC .......... *G01J 5/0025* (2013.01); *A61B 5/0077* (2013.01); *A61B 5/015* (2013.01); *G06T 7/0016* (2013.01); *G01J 2005/0077* (2013.01); *G06T 2207/10016* (2013.01); *G06T 2207/10048* (2013.01)

(58) Field of Classification Search
CPC .. H01S 3/0085; H01S 3/1068; H01S 3/13017; H04B 10/505; H04B 10/508; H04L 9/3297; G01N 15/0205; G01J 2005/0077; G01J 3/0229
See application file for complete search history.

(56) References Cited

U.S. PATENT DOCUMENTS

| | | | | |
|---|---|---|---|---|
| 5,287,183 A | * | 2/1994 | Thomas | .................. H04N 5/217 348/571 |
| 6,323,486 B1 | | 11/2001 | Grossman et al. | |
| 2012/0249782 A1 | * | 10/2012 | Oda | ........................ G03B 42/00 348/135 |
| 2016/0202164 A1 | * | 7/2016 | Trainer | .............. G01N 15/0211 356/336 |

(Continued)

OTHER PUBLICATIONS

X. Gu, G. Karunasiri, G. Chen, U. Sridhar, and B. Xu, "Determination of thermal parameters of microbolometers with a single electrical measurement," Appl. Phys. Lett., vol. 72, 1998.

(Continued)

*Primary Examiner* — Shervin K Nakhjavan
(74) *Attorney, Agent, or Firm* — Richard J. Kim

(57) ABSTRACT

An apparatus to measure the time constant of microbolometer-type uncooled thermal imaging camera pixels on a per-pixel basis has been developed. The apparatus utilizes a longwave infrared laser and acousto-optic modulator as a periodic light source to excite the pixels of the camera's focal plane array. The image frames captured by the camera during excitation are then processed and the data fit using the algorithms developed to find the time constant for each pixel in the array.

22 Claims, 5 Drawing Sheets

(56) References Cited

U.S. PATENT DOCUMENTS

2018/0270435 A1* 9/2018 Chow ................ G01N 15/1404

OTHER PUBLICATIONS

F. Utermöhlen and I. Herrmann, "Model and measurement technique for temperature dependent electrothermal parameters for microbolometer structures," 2013 Symposium on Design, Test, Integration, and Packaging of MEMS/MOEMS (DTIP), 2013.

A. J. Syllaios, M. J. Ha, W. L. McCardel, and T. R. Schimert, "Measurement of thermal time constant of microbolometer arrays," Proc. SPIE, vol. 5783, 2005.

P. Lambkin, N. Folan, and B. Lane, "Simple technique for the measurement of thermal time constants of microbolometer structures," Proc. IEEE 1999 Int. Conf. on Microelectronic Test Structures, vol. 12, 1999.

R. Blackwell, D. Lacroix, T. Bach, J. Ishii, S. Hyland, T. Dumas, S. Carpenter, S. Chan, and B. Sujlana, "17 μm FPA technology at BAE Systems," Proc. SPIE, vol. 7298, 2009.

F. Généreux, B. Tremblay, M. Girard, J. Paultre, F. Provençal, Y. Desroches, H. Oulachgar, S. Ilias, and C. Alain, "On the figure of merit of uncooled bolometers fabricated at INO," Proc. SPIE, vol. 9819, 2016.

Z. Xu, L. N. Phong, and T. D. Pope, "Performance prediction and characterization of highly insulated microbolometers for space applications," Proc. SPIE, vol. 8250, 2012.

* cited by examiner

APPARATUS AND METHOD TO PERFORM PER-PIXEL MICROBOLOMETER CAMERA TIME CONSTANT MEASUREMENTS

GOVERNMENT INTEREST

The invention described herein may be manufactured, used, sold, imported, and/or licensed by or for the Government of the United States of America.

FIELD OF THE INVENTION

This invention relates to characterization of microbolometer-type uncooled thermal imaging cameras, specifically measuring the pixel's time constant.

BACKGROUND OF THE INVENTION

Microbolometer cameras are a common type of thermal sensor, often referred to as an "uncooled sensor," where the sensor generally operates at ambient temperature conditions and produces imagery sensing typically longwave infrared (LWIR) radiation (wavelengths of about 7-14 µm). Such sensors are frequently characterized in terms of their Figure of Merit (FOM). FOM is the product of noise equivalent difference temperature (NEΔT) and time constant (TC or elsewhere τ). NEΔT is a measure of the sensitivity of the camera, while TC is a measure of the speed of response of the system. Methods for measuring and reporting NEΔT per-pixel are well known, but measurements of TC at the camera or system level have been limited to a single value for the entire focal plane array (FPA) or a large region thereof. No prior U.S. patents are known to exist for TC measurement apparatuses or methods.

Prior art allows one to measure per-pixel TCs only if one has direct electrical control of the FPA and readout integrated circuit (ROIC), which is not typically available on the camera or sensor system level. These methods tend to produce results different from those when the camera is measured at the system level and thus are not generally reflective of values in application use, limiting the measurement's value. See X. Gu, G. Karunasiri, G. Chen, U. Sridhar, and B. Xu, "Determination of thermal parameters of microbolometers with a single electrical measurement," Appl. Phys. Lett., vol. 72, 1998. See also F. Utermohlen and I. Herrmann, "Model and measurement technique for temperature dependent electrothermal parameters for microbolometer structures," 2013 Symposium on Design, Test, Integration, and Packaging of MEMS/MOEMS (DTIP), 2013. See also A. J. Syllaios, M. J. Ha, W. L. McCardel, and T. R. Schimert, "Measurement of thermal time constant of microbolometer arrays," Proc. SPIE, vol. 5783, 2005. See also P. Lambkin, N. Folan, and B. Lane, "Simple technique for the measurement of thermal time constants of microbolometer structures," Proc. IEEE 1999 Int. Conf. on Microelectronic Test Structures, vol. 12, 1999.

If direct electrical control of the FPA and ROIC is not available, the FPA must be excited optically and data can only be gathered at the frame rate of the camera. However, the frame rate of the camera is typically too slow to provide appropriate data to extract the TC (typically 30 Hz frame rate, i.e. data every 33.3 ms; typical TC about 10 ms). Techniques taking advantage of the spatial properties of the FPA and a slowly modulated source can be used to extract a TC for the entire FPA (or large region). These techniques suffer from optical distortion, non-uniformity, and both spatial and temporal noise introduced by the system. See R. Blackwell, D. Lacroix, T. Bach, J. Ishii, S. Hyland, T. Dumas, S. Carpenter, S. Chan, and B. Sujlana, "17 µm FPA technology at BAE Systems," Proc. SPIE, vol. 7298, 2009.

Other techniques use a faster modulated source and some various temporal effects. The apparatus and method detailed herein are a novel extension of this fast-modulated technique to enable TC to be measured for each pixel individually with extremely high accuracy and at various thermal operating points. No known prior work claims the ability to provide per-pixel results. See F. Généreux, B. Tremblay, M. Girard, J. Paultre, F. Provencal, Y. Desroches, H. Oulachgar, S. Ilias, and C. Alain, "On the figure of merit of uncooled bolometers fabricated at INO," Proc. SPIE, vol. 9819, 2016. This work uses a blackbody source with a mechanical shutter which closes with a variable delay with respect to readout integration period, and requires direct control of the ROIC which is not typically available at the system or camera level. In using a variable delay, they are able to build a data set with data points spaced more closely in time than their sample rate would otherwise allow, as is done herein, but with a different technique. See also Z. Xu, L. N. Phong, and T. D. Pope, "Performance prediction and characterization of highly insulated microbolometers for space applications," Proc. SPIE, vol. 8250, 2012. This work uses a mechanically chopped laser to excite small regions of the FPA and a fundamentally different method of extracting TC, using ratios of the responsivity at two different chopping frequencies.

SUMMARY OF THE INVENTION

The exemplary embodiments of this invention feature a method of exciting a response from a microbolometer or other LWIR camera and recording data frames and high precision timestamps for the purpose of measuring TC of each camera pixel in the FPA individually. The excitation is provided by a laser source which is modulated to a highly periodic square wave by an acousto-optic modulator (AOM). The source is expanded such that it is larger than the camera field of view and converted from a Gaussian intensity profile to a nearly uniform intensity profile with a series of refractive optical elements. A closed loop controller is used to ensure that the laser power remains stable over time.

The apparatus is camera-limited in terms of timing error. Both clock drift and jitter are reduced nearly to elimination by a low-drift frequency standard, precision clock generator, and a device which generates extremely low jitter timestamps for each data frame from the camera. This frequency standard is also used to ensure the source square wave period is highly stable in time.

These features combine to form an apparatus which is capable of accurately measuring TC for each camera pixel at the camera or system level. Extremely short TCs (much shorter than the typical 8-12 ms) can be measured without significant degradation in measurement accuracy—apparatus which rely on mechanical modulation of the source are typically limited in the fastest TC they can resolve with reasonable accuracy.

BRIEF DESCRIPTION OF THE DRAWINGS

Additional advantages and features will become apparent as the subject invention becomes better understood by reference to the following detailed description when considered in conjunction with the accompanying drawings wherein.

DETAILED DESCRIPTION

The drawings referred to herein and the descriptions below are meant to be exemplary of the present invention, but not limit the scope of the present invention.

Figure 1:
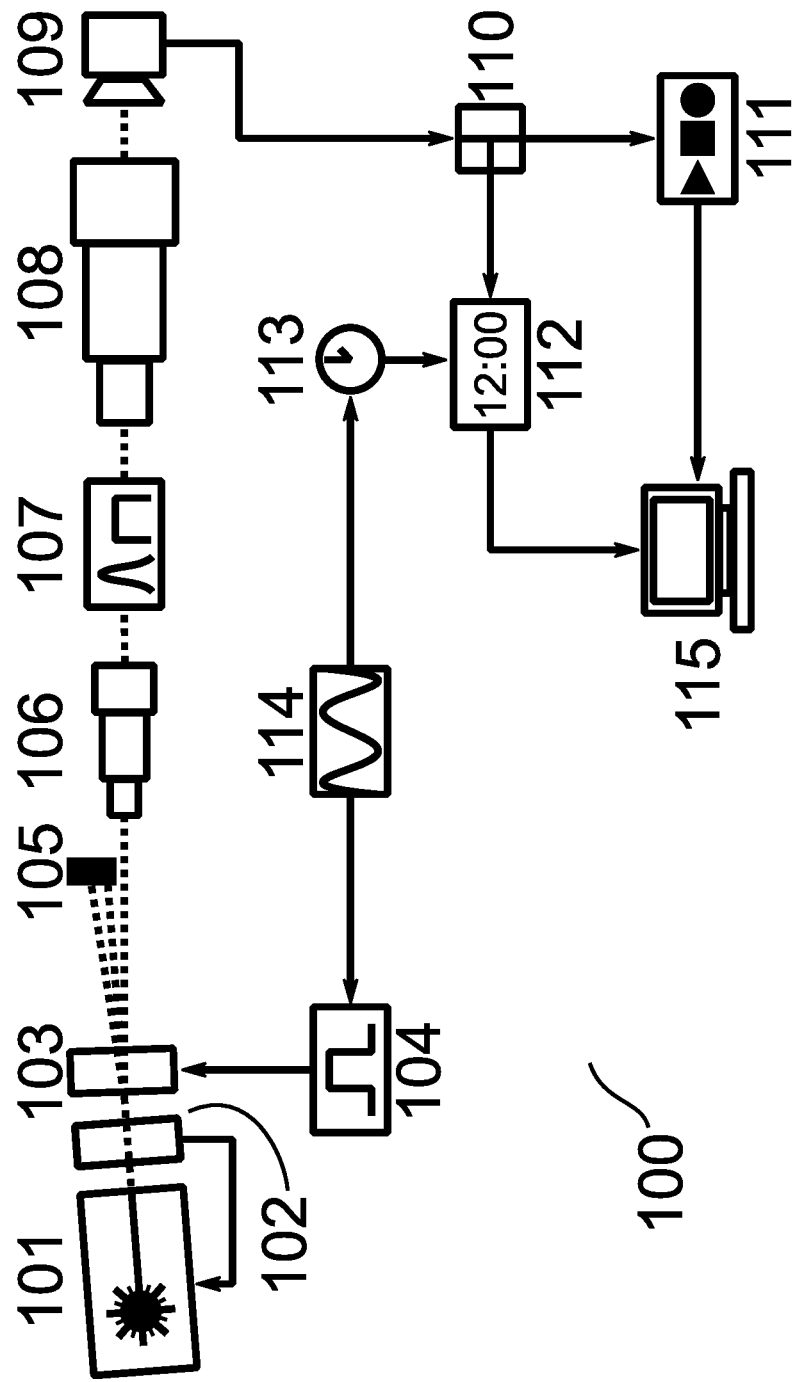
FIG. 1 shows a schematic of an exemplary per-pixel TC measurement apparatus.

An apparatus measures the time constant of microbolometer-type uncooled thermal imaging camera pixels on a per-pixel basis has been developed. The apparatus utilizes a longwave infrared laser and acousto-optic modulator as a periodic light source to excite the pixels of the camera's focal plane array. FIG. 1 shows a schematic diagram of the apparatus, 100, to gather appropriate data from which a TC can be extracted for each pixel of a camera under test. This apparatus is comprised of a source, 101-108; the camera under test, 109; and the data collection hardware, 110-115. The image frames captured by the camera during excitation are then processed and the data fit using the algorithms developed to find the time constant for each pixel in the array.

As exemplified in FIG. 1, said measurement apparatus 100 is shown comprised of a laser source; a closed loop laser line tracker to stabilize the laser source; an AOM with radio frequency driver to modulate the source laser beam; a waveform generator to provide a square wave to the AOM to modulate the source laser beam; a beam block to block the undesired order −1 and 0 laser beams; a series of refractive optics forming a collimating beam expander to appropriately size the order 1 laser beam; a series of refractive optics forming a beam expander to size the order 1 laser beam to be larger than the input of the camera; an appropriate camera, sensor, or system as the device under test; a video splitter to replicate and split the camera digital signal; a DVR to record the digital video signal; a time tagger device to generate timestamps for each data frame; a clock pulse generator to provide an accurate time reference signal to the time tagger device; a frequency standard to discipline the clock pulse generator and waveform generator; and a PC to process the data generated. Depicted as optional, said measurement apparatus 100 may include a series of refractive optical elements to act as a flat-topper to convert the order 1 laser beam from a Gaussian to near-uniform intensity profile.

Various alternative features within the scope of said exemplary apparatus 100 are set forth below:

Another type of source can be used, including, but not limited to, another type of laser, a light emitting diode (LED), or a blackbody source.

The laser line tracker can be run in open-loop mode, or another method or device can be used to stabilize the laser power, or this functionality can be omitted.

Another method or device can be used to modulate the laser source beam, or a pulsed laser is used.

A type of waveform other than a square wave can be used to modulate the source laser beam.

Another method of disposing or blocking unwanted beam orders can be used, or this functionality is omitted.

The optical elements to expand and collimate the beam can be replaced by single elements or other collections of optical elements, possibly including diffractive elements, performing significantly the same function.

Another method can be used to convert the intensity profile of the order 1 laser beam from Gaussian to a near-uniform or other intensity profile, or this functionality is omitted.

The laser beam need not be expanded to completely fill the field of view of the camera.

The camera need not be based on microbolometer technology, but still has a TC associated with its response to scene temperature changes.

The camera data need not be replicated and split.

The frame times can be recorded by the DVR instead of being generated with a time tagger or similar device, or wherein timestamps are generated by a device other than a time tagger.

The frame times need not be explicitly recorded, but rather generated based on some assumed value or other source, such as the frame rate of the camera.

The timestamps can be applied to data at other than the frame level, e.g. a timestamp is given to each data row or each pixel individually.

The external clock pulse generator or the frequency standard or an external clock pulse generator and frequency standard can be omitted or used in some other combination.

Figure 2:
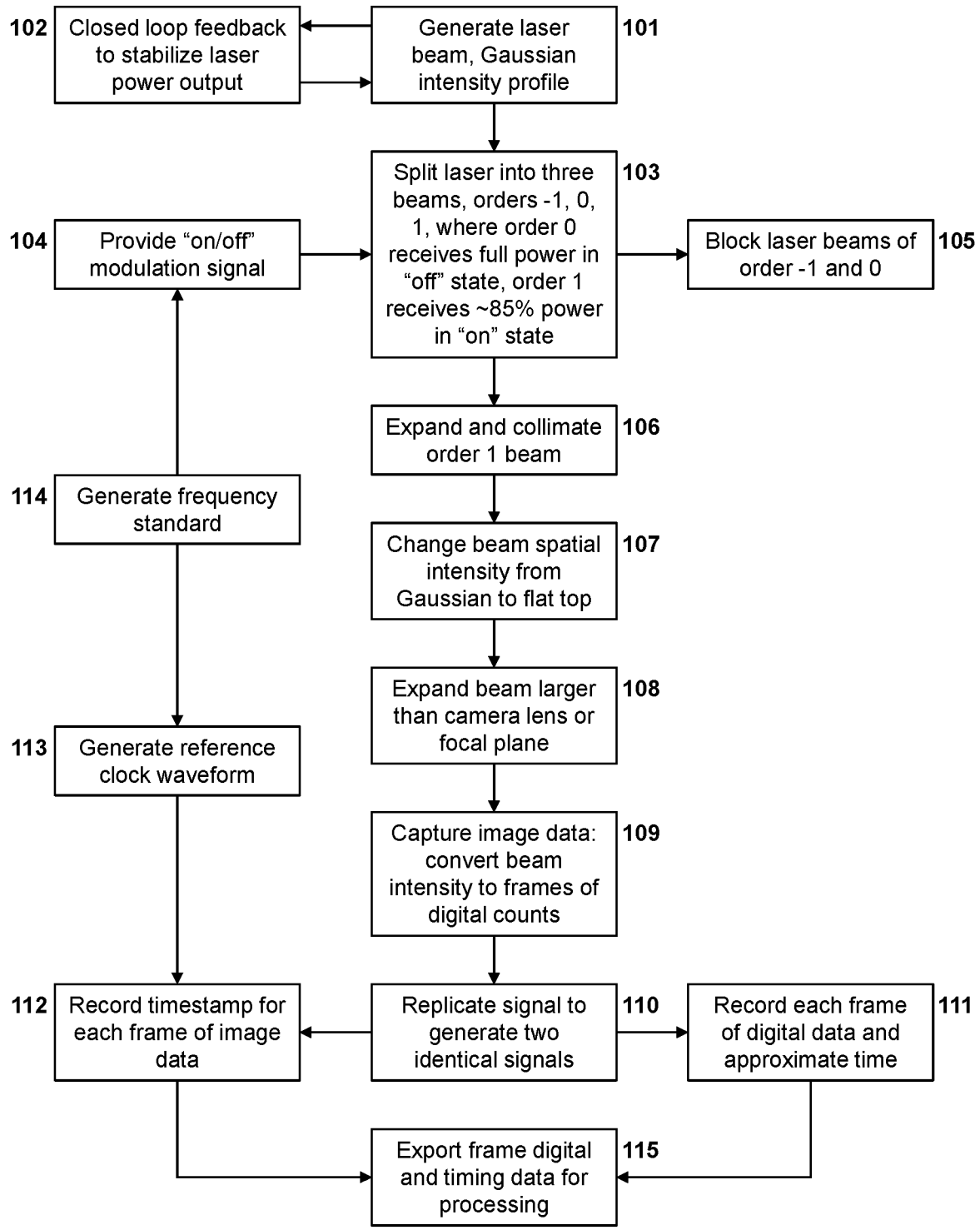
FIG. 2 shows an exemplary measurement block diagram as it relates to the measurement apparatus in FIG. 1.

FIG. 2 shows a block diagram which serves to further illustrate the description of FIG. 1 below.

The source is comprised of a $CO_2$ LWIR laser 101 which outputs a source beam with a Gaussian intensity profile. A closed loop laser line tracker 102 is used to ensure power stability over time. An AOM with radio frequency (RF) driver 103 is used to modulate the beam by diffractively splitting source beam into three beams called orders "−1," "0," and "1". All power is in the order 0 beam when the AOM is "off," i.e. no power is diffracted, and approximately 85% of the power is diffracted to the order 1 beam when the AOM is "on," with the balance of power in the order −1 and 0 beams. The AOM is controlled by a waveform generator 104 or similar which causes the AOM to modulate the order 1 beam into a highly periodic square wave with arbitrary duty cycle. The square wave period should be about five to ten times the expected TC, and not be phase synchronized to the camera frame rate. The unwanted order −1 and 0 beams are blocked or discarded by a beam block 105. A series of refractive optics forms a collimating beam expander 106 to appropriately size the order 1 laser beam width for input into a "flat-topper" 107. The flat-topper is a series of refractive optical elements which converts the beam intensity profile from Gaussian to uniform or "top-hat" shaped, i.e. the laser is of roughly uniform intensity radially out from the center of the beam until it rapidly diminishes. Strictly speaking, this component is not required so long as all pixels are illuminated to provide high enough signal to noise without any pixels receiving so much illumination that they become damaged. But, maintaining better uniformity of illumination across the array ensures more accurate and consistent results. Another series of optical elements forms a second beam expander 108 which makes the now uniform beam large enough to illuminate the entire camera field of view.

The camera under test 109 produces frames of data, i.e. video imagery, at its frame rate, typically 30-60 Hz. The data represents the camera's response to the excitation provided by the source 101-108 discussed in the previous paragraph. This digital signal is replicated and split using a video splitter 110. One data stream goes on to be recorded by a digital video recorder (DVR) 111 at full bit depth and resolution. The other data stream is used to trigger the generation and recording of one timestamp per frame by a time tagger 112. The error (jitter and drift) of the timestamp is reduced by using an external clock pulse generator 113 which is disciplined by a frequency standard 114. The same frequency standard is also used to discipline the waveform generator 104 to ensure a highly periodic and time-stable square wave to control the AOM 103. Digital video frame data and timestamps are then exported to a personal computer (PC) 115 for further processing.

Figure 4A:
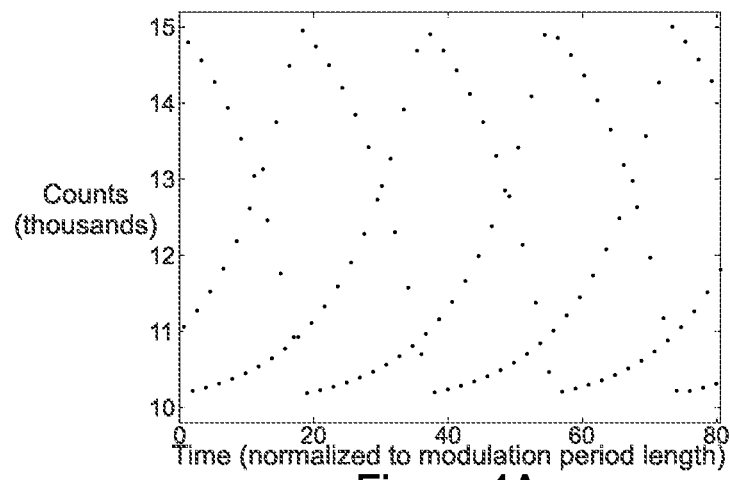
FIG. 4A shows an exemplary set of simulated data for a single pixel with no noise as collected over 80 modulation periods.
Figure 4B:
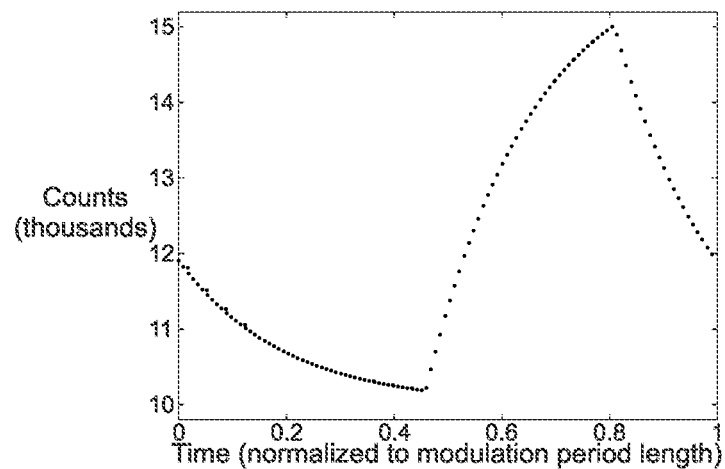
FIG. 4B shows the data "folded" back into a length of time equal to one modulation period.
Figure 4C:
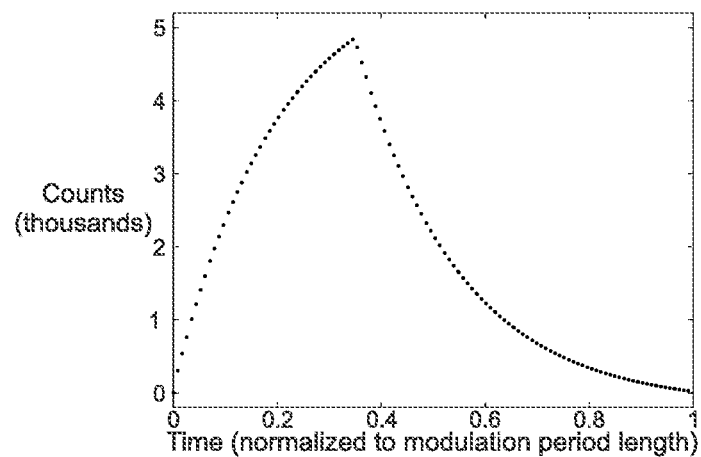
FIG. 4C shows the data in FIG. 4B circularly shifted such that the rising exponential data and decaying exponential data are contiguous.
Figure 4D:
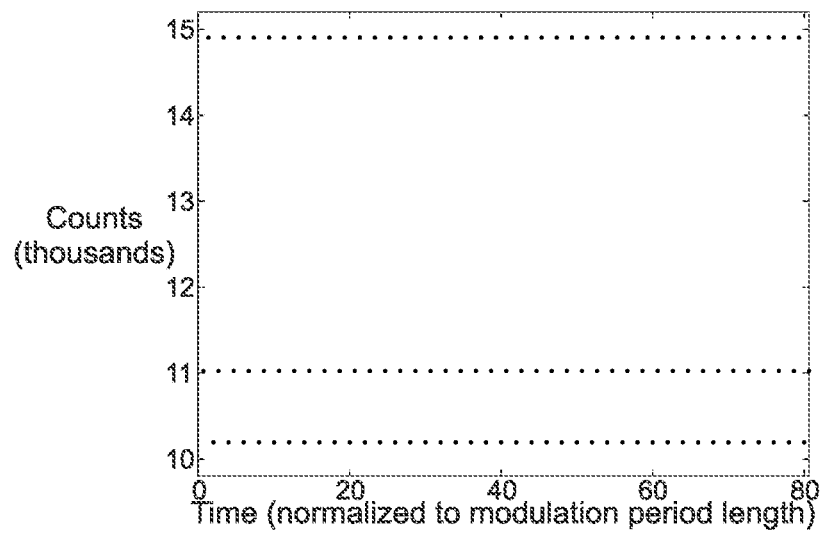
FIG. 4D shows an exemplary data set as collected over 80 modulation periods to demonstrate a problem in carelessly choosing a modulation period.
Figure 4E:
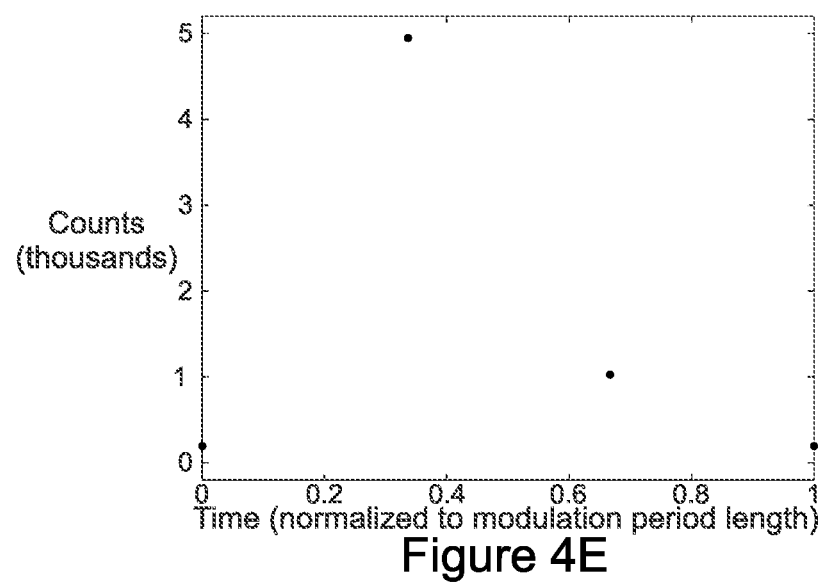
FIG. 4E is the exemplary data in FIG. 4D which has been folded, shifted, and zeroed.

FIGS. 4A-4E show an exemplary set of simulated data for a single pixel with no noise. Specifically, FIG. 4A shows data as collected over 80 modulation periods. FIG. 4B shows the data in FIG. 4A "folded" back into a length of time equal to one modulation period. FIG. 4C shows the data in FIG. 4B circularly shifted such that the rising exponential data and decaying exponential data are contiguous. The minimum value of the data series has also been subtracted from the entire series to "zero" it. FIGS. 4D and 4E demonstrate the problem resulting from carelessly choosing the modulation period. FIG. 4D shows data as collected over 80 modulation periods. FIG. 4E is the data in FIG. 4D which has been folded, shifted, and zeroed.

Figure 3:
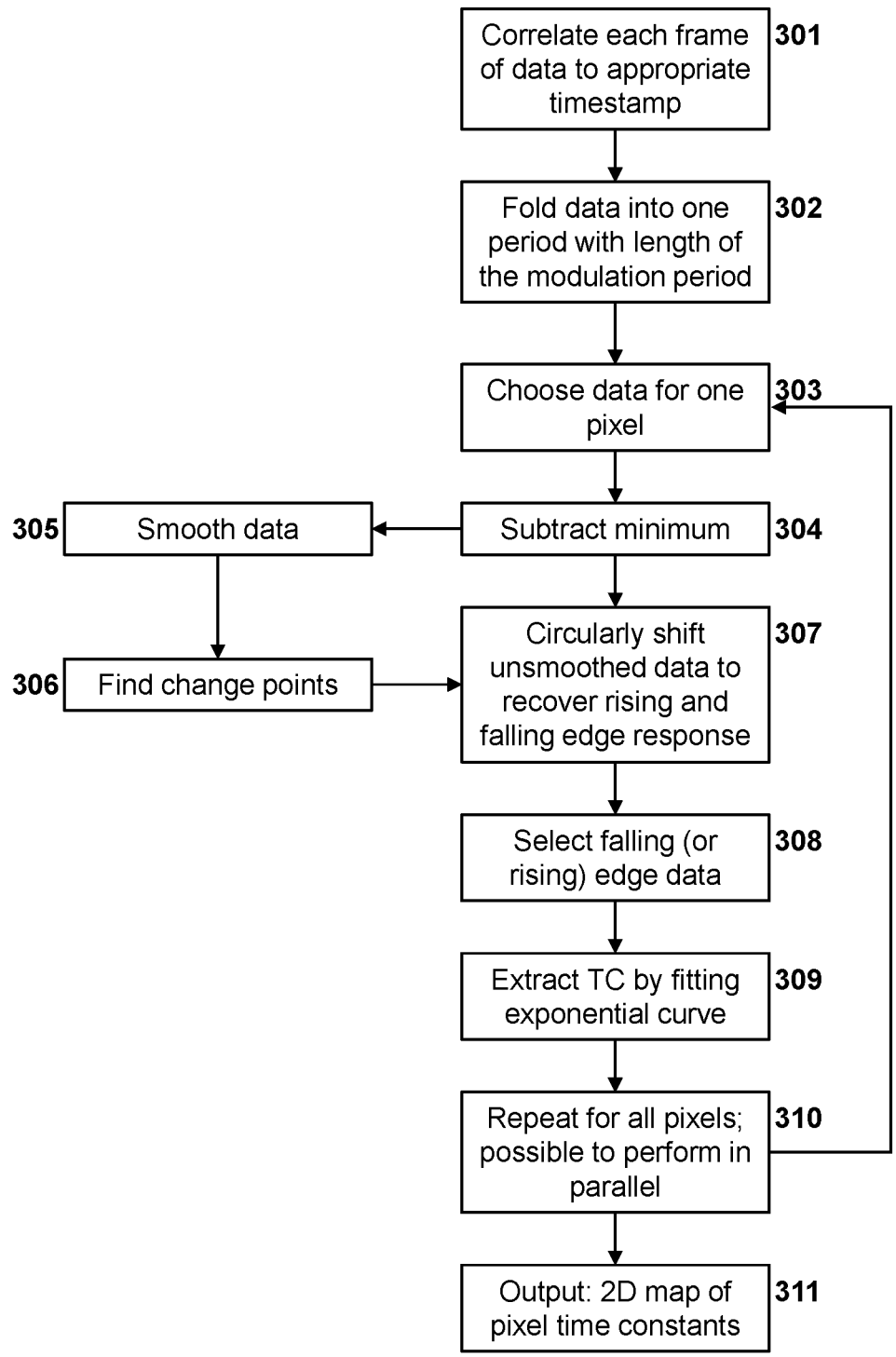
FIG. 3 shows an exemplary method to extract the TC for each pixel from the data gathered with the apparatus shown in FIG. 1 and the measurement described in FIG. 2.

Now referring to FIG. 3, the data is processed to extract a TC from each pixel. First, each video frame is correlated to the appropriate timestamp 301; see example data in FIG. 4A. Next, the data is "folded" in time such that it now occurs in the time of a single modulation period 302; see example in FIG. 4B. This can be done by first generating a new timestamp for each frame by performing modulus division on the value of each frame's timestamp by the length of the modulation period. Now, the order of the data frames is sorted by the value of its new timestamp. Next, all data in time for a single pixel is chosen 303 and the minimum value of this array of values is subtracted from the entire array of values 304. This data is smoothed (e.g. with a low-pass or other filter) 305 to remove noise and the "change points" are found 306. Change points are the points at which the exponential shape of the data inverts, i.e. from a rising exponential to a decaying exponential or vice versa. The unsmoothed data is now circularly shifted 307 (a data point is removed from the end of the array and is added to the front of the array) until the rising and decaying edge data are contiguous (i.e. the rising edge starts at time equals zero); see example in FIG. 4C based on these change points. As can be seen in FIGS. 4D and 4E, it is important to choose the modulation period carefully. The camera, sampling the bolometer response at the frame rate, should sample a sufficient set of points in the bolometer response to perform a reasonable curve fit. If the period is chosen such that the camera samples are close to the same times relative to the start of each modulation period (FIG. 4D), data points will become bunched on top of each other when folded (FIG. 4E) and will not provide appropriate data for fitting.

The falling edge data is then selected 308 (rising edge data can also be used with appropriate experimental optimization) and the TC is then extracted by, for example, fitting the data to an exponential function 309. The fit equation is given by:

$$y = a + b\exp\left[\frac{c-t}{\tau}\right] \quad (1)$$

where y is the data values in counts, a is an offset or asymptotic level, b is related to the amplitude, c is an offset in time, t is time, and $\tau$ is the time constant. This is repeated, perhaps in parallel, for every pixel in the frame 310 to produce a two-dimensional map of TCs, one for each pixel 311. Note that this apparatus, using a similar method, in addition to extracting a single first order TC as shown in (1), can extract additional parameters such as a second TC or integration times for integrators (when present), assuming the rise/fall time of the laser pulse is fast compared to the parameter of interest. This is because the time response of the camera system for each pixel so generated is the response due to the known rectangular laser illumination time function and the system transfer function relates the input to the output. For illustrative purposes, Equation 1 assumes the transfer function is a simple first order low pass filter.

In summary, an exemplary method for measuring TC for each pixel in a camera's FPA comprises a) generating appropriate video data frames and timestamps; b) correlating each frame of data to the appropriate timestamp; c) folding the data back into the span of time of one period of the source modulation; d) selecting the data for all times for a single pixel; e) subtracting the minimum value of the pixel time series from all values in the time series; f) smoothing the data; g) finding the change points of the data, i.e. where the response changes from a rising exponential to a decaying exponential and vice versa; h) circularly shifting the unsmoothed data such that the rising exponential response data and decaying exponential response data are contiguous; i) selecting decaying exponential response data; j) extracting a time constant by fitting the selected data; and k) selecting data for all times for another pixel; and repeating above steps e-j for all pixels to generate a two-dimensional map of pixel time constants.

Various alternative features within the scope of said exemplary method for measuring TC for each pixel in a camera's FPA are set forth below:

Timestamp data can be correlated to something other than a frame, e.g. a row or individual pixel, or a timestamp is generated based on assumed values instead of recorded.

The minimum value of the pixel time series need not be subtracted from all values in the time series, or some other simple method is used to process the data (e.g. subtraction of the mean).

The data need not be smoothed before finding change points.

The decaying exponential response data can be selected without finding change points or circularly shifting the data.

The rising exponential response data can be used instead of decaying exponential response data.

The TC can be extracted from the data by some other method.

The TC extraction for each pixel can happen in a parallel instead of serial (i.e. looped) fashion.

The TC can be extracted per pixel for only part of the FPA (e.g. if the entire camera field of view is not filled with the source), or the results are averaged across multiple pixels.

Many modifications and variations of the present invention are possible in light of the above teachings. It is therefore understood that within the scope of the appended claims, the invention may be practiced otherwise than described.

What is claimed is:

1. An apparatus for gathering appropriate data from which TC can be extracted for each pixel, comprising:
    a laser source to output a source laser beam;
    a closed loop laser line tracker disposed to stabilize the laser source;
    an AOM with radio frequency driver disposed to modulate the source laser beam into orders −1, 0, and 1 laser beams, wherein said order 1 laser beam is the desired modulated beam and orders −1 and 0 laser beams are undesired laser beams;
    a waveform generator to provide a square wave control to the AOM modulating the source laser beam;
    a beam block to block the undesired order −1 and 0 laser beams;
    a collimating beam expander to appropriately size the order 1 laser beam;
    a beam expander to expand the order 1 laser beam as an expanded beam larger than the input of the camera;
    a camera device under test directed to image said expanded beam and output a camera digital signal;
    a video splitter to replicate and split the camera digital signal into a digital video signal and other data stream;
    a DVR to record the digital video signal and output digital video frames;
    a time tagger device to generate timestamps for each data frame of other data stream;
    a clock pulse generator to provide an accurate time reference signal to the time tagger device to generate timestamps;
    a frequency standard to discipline the clock pulse generator and said waveform generator; and
    a PC to process data generated from said digital video frames and timestamps.

2. The apparatus as recited in claim 1, wherein said laser source is based on a laser emitter, a light emitting diode, or a blackbody source.

3. The apparatus as recited in claim 1, wherein the laser line tracker is run in open-loop mode.

4. The apparatus as recited in claim 1, wherein a pulsed laser beam is used.

5. The apparatus as recited in claim 1, wherein said collimating beam expander is comprised of a series of refractive optics forming a beam expander to appropriately size the order 1 laser beam.

6. The apparatus as recited in claim 1, wherein said beam expander is comprised of a series of refractive optics forming a beam expander to size the order 1 laser beam as an expanded beam larger than the input of the camera.

7. The apparatus as recited in claim 1, comprising a series of refractive optical elements to act as a flat-topper directed to convert the order 1 laser beam from a Gaussian to near-uniform intensity profile or other intensity profile.

8. The apparatus as recited in claim 1, wherein the laser beam is not expanded to completely fill the field of view of the camera device.

9. The apparatus as recited in claim 1, wherein the camera device has a TC associated with its response to scene temperature changes, and can be based on microbolometer technology.

10. The apparatus as recited in claim 1, wherein said camera device under test is either a camera, a sensor, or an imaging system, wherein the camera digital signal need not be replicated and split.

11. The apparatus as recited in claim 1, wherein frame times are recorded by the DVR instead of being generated with a time tagger or similar device.

12. The apparatus as recited in claim 1, wherein frame times are not explicitly recorded, but rather generated based on some assumed value or other source, such as the frame rate of the camera.

13. The apparatus as recited in claim 1, wherein a timestamp is given to each data row or each pixel individually.

14. The apparatus as recited in claim 1, wherein a signal processing device is used to process the data.

15. A method for measuring TC for each pixel in a camera's FPA using the apparatus for gathering appropriate data according to claim 1, the method for measuring TC for each pixel in a camera's FPA comprising the steps of:
    a) receiving by said PC data generated from said digital video frames and timestamps;
    b) correlating each frame of data to a timestamp as data;
    c) folding the data back into a span of time of one period of the source laser beam modulation;
    d) selecting the data for all times for a single pixel;
    e) subtracting a minimum value of pixel time series from values in the time series as subtracted data;
    f) smoothing the subtracted data as smoothed data;
    g) finding change points of the smoothed data;
    h) circularly shifting the subtracted data passed as unsmoothed data such that rising exponential response data and decaying exponential response data are contiguous;
    i) selecting decaying exponential response data as selected data;
    j) extracting a time constant by fitting the selected data; and
    k) selecting data for all times for another pixel and repeating said steps e) through j) for all pixels to generate a two-dimensional map of pixel time constants for output or display from said PC.

16. The method for measuring TC for each pixel in a camera's FPA as recited in claim 15, wherein a timestamp is correlated to a row or individual pixel, or a timestamp is generated based on assumed values.

17. The method for measuring TC for each pixel in a camera's FPA as recited in claim 15, wherein the subtracted data is based on a method of subtraction of the mean.

18. The method for measuring TC for each pixel in a camera's FPA as recited in claim 15, wherein said finding change points is based on the subtracted data that is not smoothed.

19. The method for measuring TC for each pixel in a camera's FPA as recited in claim 15, wherein the decaying exponential response data is selected without finding change points or circularly shifting the data.

20. The method for measuring TC for each pixel in a camera's FPA as recited in claim 15, wherein rising exponential response data is selected instead of decaying exponential response data.

21. The method for measuring TC for each pixel in a camera's FPA as recited in claim 15, wherein said extracting a time constant for each pixel happens either in parallel or serially.

22. The method for measuring TC for each pixel in a camera's FPA as recited in claim 15, wherein said extracting a time constant per pixel is for a portion of the FPA of a source in a camera field of view, or results are averaged across multiple pixels.

* * * * *